United States Patent
Zhang et al.

(10) Patent No.: US 9,513,260 B2
(45) Date of Patent: Dec. 6, 2016

(54) METHODS, SYSTEMS AND APPARATUS OF AN ALL-OPTICS ULTRASOUND SENSOR

(71) Applicant: Northwestern University, Evanston, IL (US)

(72) Inventors: Hao F. Zhang, Deerfield, IL (US); Cheng Sun, Wilmette, IL (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 166 days.

(21) Appl. No.: 14/299,807

(22) Filed: Jun. 9, 2014

(65) Prior Publication Data

US 2014/0360273 A1    Dec. 11, 2014

Related U.S. Application Data

(60) Provisional application No. 61/832,508, filed on Jun. 7, 2013.

(51) Int. Cl.
    *G01N 29/06*      (2006.01)
    *G01N 29/34*      (2006.01)
    (Continued)

(52) U.S. Cl.
    CPC ...... *G01N 29/0681* (2013.01); *G01N 21/1702* (2013.01); *G01N 29/14* (2013.01);
    (Continued)

(58) Field of Classification Search
    CPC   G01N 29/0681; G01N 21/1702; G01N 29/14; G01N 29/2418; G01N 29/34; G01N 2291/0246; G02B 6/12007; G02B 6/1221; G02B 21/0004
    (Continued)

(56) References Cited

U.S. PATENT DOCUMENTS

| 2004/0114899 A1* | 6/2004 | Mattsson | G02B 6/12007 385/129 |
| 2005/0286602 A1* | 12/2005 | Gunn | H01S 5/142 372/94 |

(Continued)

OTHER PUBLICATIONS

International Bureau, "International Preliminary Report on Patentability", issued in connection with PCT patent application No. PCT/US2014/041556, mailed on Dec. 17, 2015, 10 Pages.

(Continued)

*Primary Examiner* — Laura Martin
*Assistant Examiner* — Rose M Miller
(74) *Attorney, Agent, or Firm* — Hanley, Flight and Zimmerman, LLC (57) ABSTRACT

Certain examples provide a transparent ultrasonic transducer including a transparent substrate and a transparent optical resonator positioned on the transparent substrate. The transparent optical resonator is to facilitate excitation of a biological sample and to receive acoustic emission from the biological sample triggered by the excitation, for example.

Certain examples provide a ring resonator ultrasonic detector including a microscope cover slide. The microscope cover sheet includes a substrate and a ring optical resonator positioned on the substrate. The example ring optical resonator is to facilitate illumination of a biological sample and to receive acoustic emission from the biological sample in response to the illumination.

17 Claims, 7 Drawing Sheets

(51) Int. Cl.
  G01N 29/14    (2006.01)
  G01N 29/24    (2006.01)
  G01N 21/17    (2006.01)
  G02B 6/12     (2006.01)
  G02B 6/122    (2006.01)
  G02B 21/00    (2006.01)

(52) U.S. Cl.
  CPC ......... *G01N 29/2418* (2013.01); *G01N 29/34* (2013.01); *G01N 2291/02466* (2013.01); *G02B 6/12007* (2013.01); *G02B 6/1221* (2013.01); *G02B 21/0004* (2013.01)

(58) Field of Classification Search
  USPC .................................................. 73/606, 643
  See application file for complete search history.

(56) References Cited

U.S. PATENT DOCUMENTS

| | | | | |
|---|---|---|---|---|
| 2007/0071394 A1* | 3/2007 | Faccio | ............... | G02B 6/12007 385/131 |
| 2008/0095490 A1* | 4/2008 | Ashkenazi | ........... | A61B 5/0097 385/13 |
| 2010/0268042 A1 | 10/2010 | Wang et al. | | |
| 2012/0182552 A1* | 7/2012 | Heidrich | ............ | G01N 21/7746 356/364 |

OTHER PUBLICATIONS

International Searching Authority, "Search Report", issued in connection with International patent application No. PCT/US2014/041556, mailed on Dec. 19, 2014, 8 pages.

International Searching Authority, "Written opinion", issued in connection with International patent application No. PCT/US2014/041556, mailed on Dec. 19, 2014, 8 pages.

International Searching Authority, "Invitation to pay additional fees and, where applicable, protest fee", issued in connection with PCT application No. PCT/US2014/041556, mailed on Sep. 10, 2014, 8 pages.

Edward Z. Zhang et al., "Multimodal photoacoustic and optical coherence tomography scanner using an all optical detection scheme for 3D morphological skin imaging", Biomedical Optics Express, vol. 2, No. 8, Aug. 1, 2011, 14 pages.

Chen Sung-Liang et al, "Photoacoustic endoscopy using polymer microring resonators", Photons Plus Ultrasound: Imaging and sensing 2011, Feb. 10, 2011, pp. 1-6.

Chung-Yen Chao et al, "High-Frequency Ultrasound Sensors Using Polymer Microring Resonators", IEE Transactions on Ultrasonics, Ferroelectrics and Frequency control, IEEE, vol. 54, No. 5, May 1, 2007, pp. 957-965.

Maxwell et al., "Polymer Microring Resonators for High-Frequency Ultrasound Detection and Imaging", IEEE Journal of Selected topics in Quantum Electronics, IEEE Service Center, vol. 14, No. 1, Jan. 1, 2008, 7 pages.

* cited by examiner

METHODS, SYSTEMS AND APPARATUS OF AN ALL-OPTICS ULTRASOUND SENSOR

CROSS-REFERENCE TO RELATED APPLICATIONS

The present application claims priority to U.S. Provisional Application No. 61/832,508, filed on Jun. 7, 2013, which is herein incorporated by reference in its entirety.

STATEMENT REGARDING FEDERALLY SPONSORED RESEARCH OR DEVELOPMENT

This invention was made with government support under RC4EY022883, RC4 EY021357, and R01 EY019951 awarded by the National Institutes of Health and CBET1055379, CBET1066776, and CMMI0955195 awarded by the National Science Foundation. The government has certain rights in the invention.

FIELD OF THE DISCLOSURE

The presently described technology generally relates to microscopy and, more specifically, to a transparent transducer to facilitate joint optical and/or acoustic imaging.

BACKGROUND

Photoacoustic imaging is a hybrid biomedical imaging modality developed based on a photoacoustic effect. The photoacoustic effect is a formation of sound waves following light absorption in a sample. In photoacoustic imaging, non-ionizing laser pulses are delivered into biological tissues. Some of the delivered energy is absorbed and converted into heat, leading to transient thermoelastic expansion and thus wideband (e.g. MHz) ultrasonic emission. Generated ultrasonic waves are then measured by ultrasonic detectors to form images. Two dimensional (2D) or three dimensional (3D) images of targeted areas can then be formed.

The figures are not to scale. Instead, to clarify multiple layers and regions, the thickness of the layers may be enlarged in the drawings. Wherever possible, the same reference numbers will be used throughout the drawing(s) and accompanying written description to refer to the same or like parts. As used in this patent, stating that any part (e.g., a layer, film, area, or plate) is in any way positioned on (e.g., positioned on, located on, disposed on, or formed on, etc.) another part, means that the referenced part is either in contact with the other part, or that the referenced part is above the other part with one or more intermediate part(s) located therebetween. Stating that any part is in contact with another part means that there is no intermediate part between the two parts.

DETAILED DESCRIPTION

Overview

Certain examples provide an optically transparent, compliant (e.g., polymeric and/or other deformable material, etc.) photonic resonator which enables low-noise, wideband detection of ultrasonic signals. Fabricating the polymeric resonator on a thin transparent substrate allows the transducer to be directly compatible with a conventional optical microscope or other optical imaging system for simultaneous optical and acoustic imaging. Using state-of-the-art nano-fabrication technique(s), an optical-based ultrasonic transducer can be fabricated at low cost. In addition, by utilizing coupled modes among multiple resonators, it is possible to reduce or eliminate a need for an expensive narrow band laser source to provide a fully integrated transducer that includes both active and passive photonic components.

In photoacoustic (PA) imaging, non-ionizing laser pulses are delivered into biological tissue (as opposed to radio frequency pulses used in thermoacoustic imaging). A portion of the delivered laser energy is absorbed by the tissue and converted to heat, which results in emission of ultrasonic waves that can be detected by one or more ultrasonic detectors and used to form an image.

Photoacoustic microscopy (PAM) uses a laser to induce acoustic pressure waves in a tissue sample to provide a depth of imaging in the tissue limited by ultrasonic attenuation. PAM does not rely on contrast agent to image optical absorption contrast in biological tissue. PAM can be used to measure several tissue physiological parameters, such as hemoglobin oxygen saturation, that would otherwise remain challenging. PAM can be used in functional imaging, for example, to detect changes in blood oxygenation, skin melanoma, etc.

Compared with other existing high-resolution optical imaging modalities, including confocal microscopy, two-photon microscopy, and optical coherence tomography, PAM can extract three-dimensional physiologically specific optical absorption properties in biological tissue at a lateral resolution that is subject only to an optical diffraction limit. In PAM, a short-pulsed laser beam is focused onto biological tissues. Absorbed laser energy leads to a transient thermoelastic expansion and, subsequently, launches ultrasonic waves containing a wide-range of frequency components, which can be detected to construct optical absorption contrast-based images. An amplitude of an induced ultrasonic wave is proportional to a product of local optical fluence and optical absorption coefficient. A traveling time of the induced ultrasonic wave is proportional to a distance between its origin and the ultrasonic detector. PAM can image either endogenous sources, such as hemoglobin and melanin, or exogenous contrast agents, such as chemical dyes, nanoparticles, and reporter gene products. A broad range of available contrast sources allows PAM to reveal anatomical and functional information, such as intracellular thermal transmission, energy difference in molecular vibrational bands, tumor angiogenesis, melanoma, brain cortex functions, water and lipid concentration, and metabolic rate of oxygen.

Additionally, integrating PAM with other optical microscopic imaging modalities provides a comprehensive tool that can simultaneously capture multiple optical contrasts in tissue, including tissue that exhibits poor optical absorption. However, previous efforts to integrate PAM with confocal microscopy and optical coherence tomography were found to have rather limited lateral and axial resolutions.

In prior approaches, lateral resolution was fundamentally limited by the small numerical aperture (NA) being used due to the long working distance required to accommodate sizeable piezoelectric detectors. Axial resolution was constrained by the finite detection bandwidth of commonly used piezoelectric detectors. Due to the limitations of these piezoelectric detectors, it becomes technically difficult to integrate PAM with a conventional high-resolution optical microscopic system in which the working distance of an objective lens is normally less than 1 mm.

However, the sizeable and opaque piezoelectric ultrasonic detectors commonly used in PAM impose a serious constraint. Although traditional piezo-electric ultrasonic transducer technologies have advanced tremendously over the past decade, these transducers still suffer from at least two key limitations: (1) opaque and relatively large size packaging and (2) limited detection bandwidth. First, traditional piezo-electric ultrasonic transducer packaging can be large because piezo-electric materials usually need backing and housing to achieve optimal performance. The final packaged size cannot be too thin, and piezo-electric materials and backing materials are not transparent to light. Moreover, due to the finite size to achieve optimal sensitivity, an existing ultrasonic transducer has a limited solid angle in a detection space, which prevents sensitive ultrasound detection from the off-axis position. As a result, for special applications such as high-resolution microscopy, ocular imaging, and endoscopy, the applicability of a piezo-electric transducer is limited. Second, a traditional ultrasonic transducer made of rigid piezo-electric materials has limited detection bandwidth that effectively restricts a saturation limit and axial resolution of photoacoustic imaging.

Second, the sensitivity of an ultrasonic transducer is determined by noise equivalent detectable pressure (NEDP). An existing traditional ultrasonic transducer typically has a NEDP around hundreds of Pascals. In order to further improve the ultrasonic detection sensitivity, certain examples provide new technology to reduce NEDP by at least one order of magnitude.

In contrast to a conversional ultrasound transducer made of rigid and mostly opaque piezoelectric materials, optical-based ultrasonic transducers utilize optically transparent polymer materials that can be easily deformed by incident ultrasonic pressure waves. The strong optical resonance magnifies a resulting refractive index change into the measurable shift in the resonance modes, which enables low-noise, wide-band detection of ultrasonic signals with a NEDP of approximately tens of Pascals. Although other attempts have been made using an optical microring resonator for ultrasonic detection, these resonators are fabricated on silicon, which causes many problems in photoacoustic imaging due to the opacity, rigidity, and strongly optical absorbing properties of the silicon.

BRIEF DESCRIPTION

Certain examples provide a transparent ultrasonic transducer including a transparent substrate and a transparent optical resonator positioned on the transparent substrate. The transparent optical resonator is to facilitate excitation of a biological sample and to receive acoustic emission from the biological sample triggered by the excitation, for example.

The example transducer can include a plurality of optical resonators coupled on the transparent substrate. The example transducer can be coupled with an optical imaging instrument to facilitate optical and acoustic imaging of the biological sample. The example optical imaging instrument can include an optical microscope, wherein the coupling of the transducer with the optical microscope converts the microscope into a photoacoustic microscope for simultaneous optical and acoustic imaging.

The example transducer can include a laser diode and a photodetector arranged with respect to the optical resonator. The example optical resonator can include a transparent ring optical resonator. The example optical resonator can be a polymeric optical resonator. The example optical resonator can be a micro-ring resonator.

The example transducer can include a waveguide coupled to the transparent optical resonator. The example transducer can include a plurality of tapered fibers to couple light in and out of the waveguide. The example transducer can include a low-dielectric gap between the transparent optical resonator and the waveguide.

The example transparent substrate can include a quartz substrate. The example transparent substrate can include a non-crystallized fused quartz substrate. The example transparent substrate and the transparent optical resonator can be arranged on a microscope cover slide.

Certain examples provide a ring resonator ultrasonic detector including a microscope cover slide. The microscope cover sheet includes a substrate and a ring optical resonator positioned on the substrate. The example ring optical resonator is to facilitate illumination of a biological sample and to receive acoustic emission from the biological sample in response to the illumination.

The example detector can further include a plurality of optical resonators coupled on the substrate. The example microscope cover slide can be coupled with an optical microscope to facilitate optical and acoustic imaging of the biological sample by converting the optical microscope into a photoacoustic microscope for optical and acoustic imaging. The example detector can further include a waveguide coupled to the ring optical resonator. The example detector can further include a plurality of tapered fibers to couple light in and out of the waveguide. The example detector can further include a low-dielectric gap between the transparent optical resonator and the waveguide.

Detailed Description of Certain Examples

Figure 1:
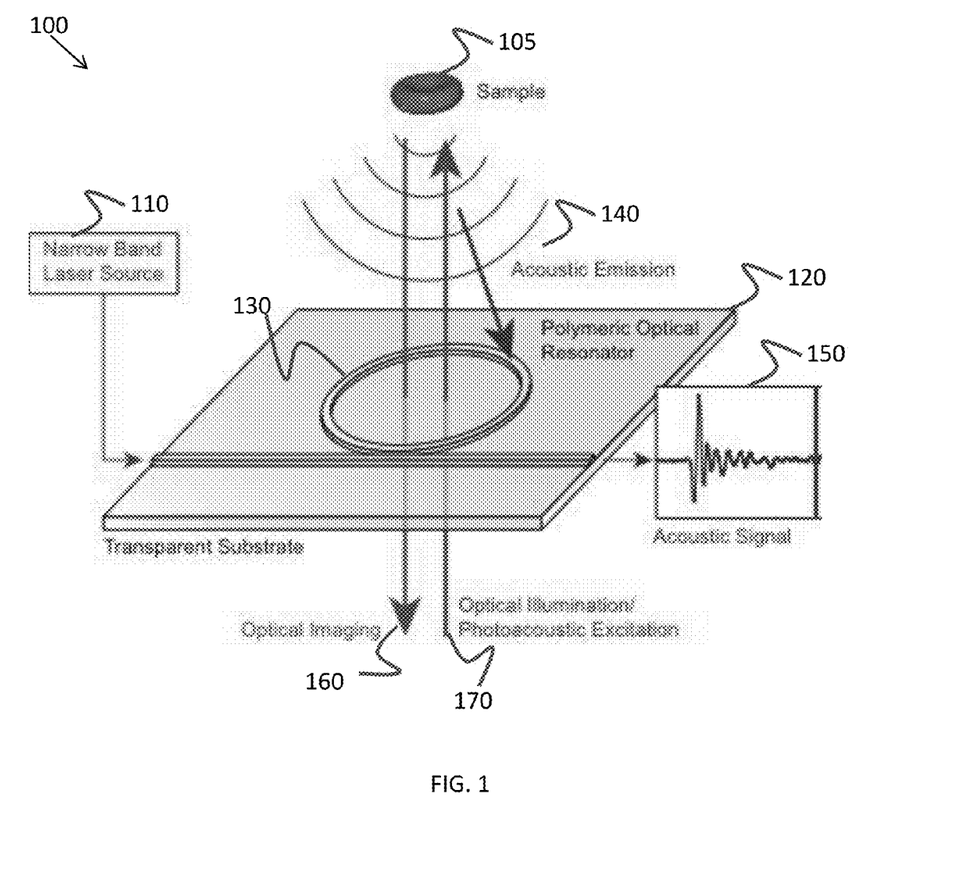
FIG. 1 illustrates an example optical and acoustic imaging system.

As shown in the example of FIG. 1, an example transparent ultrasonic transducer includes a polymeric optical resonator (e.g., a micro-ring resonator (MRR)) on a transparent substrate to enable simultaneous optical and ultrasonic imaging of biological samples. Improved or "optimal" sensitivity is obtained by placing the optical resonator at a center of an illumination/excitation beam with reduced or minimal interference to the optical imaging.

FIG. 1 provides an illustration of an example optical and acoustic imaging system 100. The example system 100 of FIG. 1 includes a narrow band laser source 110 provided to a transducer formed from a transparent substrate 120 on which a polymeric optical resonator 130 is positioned. Optical illumination (e.g., photoacoustic excitation) 170 is delivered through the substrate 120 to a sample 105, which produces an acoustic emission 140 detected by the resonator 130. An acoustic signal 150 and optical imaging output 160 are generated.

The optical ring resonator 130 allows acoustic emission 140 from the sample 105 to build up or increase in intensity over multiple round trips before outputting emission 140 of a certain resonance wavelength. The optical ring resonator 130 serves as a filter because only certain wavelengths will be at resonance within the loop. In certain examples, multiple rings can be coupled together.

In certain examples, a micro-ring resonator ultrasonic detector includes a bus waveguide and a ring-shaped waveguide separated by a low-dielectric gap. The bus waveguide provides input and output ports, and coupling to the ring waveguide is accomplished by evanescently tunneling across the low-dielectric gap. A light wave circulating inside the ring waveguide leads to a strong optical resonance supported by a whisper gallery mode (WGM). Whispering gallery waves travel around a concave surface. The resulting optical resonance can be characterized by a narrow dip in light transmitted through the bus waveguide due to deconstructive interference associated with optical resonance. In certain examples, zero transmission can be achieved when intrinsic loss of the ring resonator matches coupling loss (referred to as a critical coupling condition).

Built upon such a strong optical resonance, an MRR made from soft polymeric and/or other deformable material can be used as an ultra-sensitive detector that converts ultrasonic pressure wave-induced deformation of MRR into a measurable quantity in a shift of its optical resonance modes. The deformation causes changes in both the geometry and refractive index (RI) of the polymer MRR and subsequently alters the corresponding effective refractive index ($n_{eff}$) of the guided mode. Resulting changes in optical path length of the MRR are accumulated while the light wave is circulating inside. The amplified optical path length changes can then be quantified by measuring a wavelength shift of the resonance modes. Using a narrow-band laser source, such a resonance shift can be measured as a modulation of the transmitted optical intensity at given wavelength.

The sensitivity of detecting pressure variation using MRR can be defined as:

$$S = \frac{dT}{dP} = \frac{dn_{eff}}{dP} \frac{d\lambda_r}{dn_{eff}} \frac{dT}{d\lambda_r},\qquad\text{(Eq. 1)}$$

where T is transmission through a bus waveguide; P is an ultrasonic pressure; $\lambda_r$ is a resonance wavelength. The first term $dn_{eff}/dP$ defines a pressure-induced effective refractive index change in the polymer waveguide that takes into account the Young's modulus and elasto-optic coefficient of the polymer as well as a cross-sectional shape of the waveguide. The second term $d\lambda_r/dn_{eff}$ is a resulting shift of the resonance wavelength due to change of $n_{eff}$. The resonance wavelength can be derived from a standing wave condition of the WGM:

$$m\lambda_r = 2\pi R n_{eff}\qquad\text{(Eq. 2),}$$

where m is an order of the resonance mode, and R is a radius of the ring resonator. Considering a small perturbation in $n_{eff}$ results in:

$$\frac{d\lambda_r}{dn_{eff}} = \frac{2\pi R}{m} = \frac{\lambda_r}{n_{eff}}.\qquad\text{(Eq. 3)}$$

An improved or optimal sensitivity can be obtained at a rising or falling edge of a resonance dip. Therefore, $dT/d\lambda_r$ can be defined as a slope of its linear region, which can be approximated as linearly proportional to a Q-factor. A maximum detectable PA pressure is also constrained by a wavelength range of the linear region, which is inversely proportional to the Q-factor. Overall, the detection sensitivity can be simplified as:

$$S = A\lambda_r Q\qquad\text{(Eq. 4),}$$

where A is a design-specific parameter that is collectively determined by materials properties and guided mode profile of the polymeric bus waveguide. It can be treated as a constant for a given polymer material and cross-sectional shape of the waveguide. Therefore, an MRR with a higher Q-factor and a longer wavelength will favorably increase its ultrasonic detection sensitivity.

In certain examples, detection bandwidth is determined by a temporal response of two concurrent processes: optical resonance due to the WGM and propagation of an ultrasonic wave in surrounding media. From the perspective of optical resonance, when ultrasonic pressure induces resonance mode change, it takes time for the WGM to gradually accumulate energy to reach a steady state again. A corresponding time constant for reestablishing a steady state is comparable to an effective photon life time in resonator $\tau = Q/\omega$, where $\omega$ is an angular frequency of the light wave. When MRR is used for ultrasonic detection, a resulting resonance-limited cutoff ultrasonic frequency ($f_0$) is inversely proportional to a time constant $f_0 = 1/\tau = \omega/Q$. On the other hand, from the perspective of acoustic wave propagation, in order to avoid deconstructive interference between an incoming acoustic wave and a subsequent reflection from the surface of the rigid substrate, the thickness of the waveguide is constrained by a quasi-static limit. Since acoustic scattering by the MRR itself can be negligible, a resulting geometry-limited cutoff frequency ($f_t$) can be approximated as $f_t = v/2h$, where v is an ultrasound speed in water and h is the waveguide thickness.

A planar ultrasonic detector with finite dimension often exhibits angular-dependent sensitivity to a point PA source. For a ring-shaped detector, the angular-dependent sensitivity follows:

$$D(\theta) = J_0(kR \sin \theta)\qquad\text{(Eq. 5),}$$

where $\theta$ is an incident angle of the ultrasound wave; $J_0$ is a $0^{th}$ order Bessel function of a first kind; and $k = 2\pi f/v$ is an ultrasonic wave vector at a given ultrasound frequency f. A full-width-halfmax (FWHM) of angular-dependent sensitivity is inversely proportional to a radius of the ring resonator R; thus, a smaller MRR permits sensitive ultrasound detection over a wider incident angle, which, in turn, allows a larger field of view (FOV) in laser-scanning PAM systems.

Figure 2:
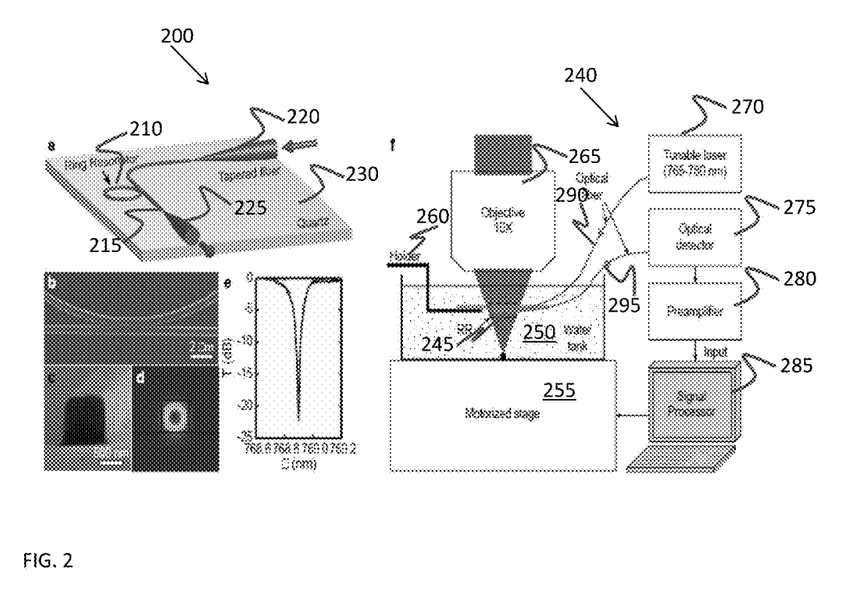
FIG. 2a illustrates an example transparent ultrasonic transducer.
FIGS. 2b-c show example scanning electronic microscope images of nano-fabricated polymeric optical resonator on a transparent substrate.
FIG. 2d depicts a simulated optical mode provider of the resonator on the substrate.
FIG. 2e shows strong optical resonance provided by the example transducer produces a sharp dip in transmission.
FIG. 2f illustrates an example system used to characterize a transparent ultrasonic transducer.

FIG. 2 illustrates an example transparent ultrasonic transducer (FIG. 2a). FIGS. 2b-c show scanning electronic microscope images of a top view (2b) and a cross-sectional view (2c) of a nano-fabricated polymeric optical resonator on a transparent substrate. FIG. 2d depicts a simulated optical mode provider of the resonator on the substrate. As shown in the graph of FIG. 2e, strong optical resonance provided by the example transducer produces a sharp dip in transmission. FIG. 2f illustrates an example system used to characterize a transparent ultrasonic transducer, for example, using a tunable laser to provide illumination to a transducer being held or positioned in a water tank, which provides emission over another optical fiber to an optical detector and a preamplifier to be input to a computer or other signal processing device to characterize the transmitting and receiving properties of the transducer.

The example transparent ultrasonic transducer 200 shown in FIG. 2a includes a micro-ring resonator 210 coupled to two tapered optical fibers 220, 225 on a quartz substrate 230 (e.g., a fused quartz substrate). The example transducer 200 can be a packaged MRR ultrasound detector, for example.

As shown in the example of FIG. 2a, a first tapered optical fiber 220 provides a laser input to the MRR 210, and a second tapered optical fiber 225 provides a laser output to the MRR 210. The two tapered fiber tips couple light in and out of a bus waveguide 230 by closely matching a mode-profile of the waveguide 230. In certain examples, the bus waveguide 230 includes a 90-degree bend to reduce or minimize cross-talk between the input and output ports 220, 225. This simplifies packaging by reducing or eliminating an intricate process of dicing the quartz substrate 230 (e.g., the non-crystallized-fused quartz substrate), and can yield better coupling efficiency due to better mode matching between the taper fiber tip 220, 225 and the polymer waveguide 230.

FIG. 2f shows an experimental PAM system 240 used to characterize a transducer formed using an optical resonator 245, such as an MRR. A testing sample is placed at the bottom of a water tank 250 mounted on a two-dimensional translational stage 255. The MRR ultrasonic detector 245 is attached to an adjustable holder 260 and immersed in water. A pulsed laser (e.g., output wavelength: 532 nm; pulse duration: 1 ns; by Elforlight Ltd) is focused onto the sample by an objective lens 265 (e.g., a 10× objective lens such as NA 0.25, by Mitutoyo) through the transparent MRR ultrasonic detector 245. A narrow band tunable laser 270 (e.g., TLB-6712, by New Focus) with an output wavelength range of 765 nm-780 nm is coupled onto a bus waveguide through a tapered fiber 290. The transmitted light is collected by another tapered fiber 295 and measured by an avalanche photodetector 275 (e.g., APD, bandwidth: 5 MHz-1 GHz, APD210, by Menlo Systems). The detected signal can be amplified by a preamplifier 280 (e.g., a 28 dB amplifier such as ZFL500NL1, Mini-circuits; bandwidth: 10 MHz-500 MHz) and digitized by a computer-based data acquisition system 285 (e.g., a CobraMax high-speed PCI digitizer, GaGe). PA signals are detected by capturing changes in transmission intensity of MRR caused by ultrasound-induced deformation. An optical axis of the PA illumination is aligned with a center of the MRR 245, and PA imaging can be obtained by raster-scanning the sample while the MRR ultrasonic detector is kept stationary, for example.

Figure 3:
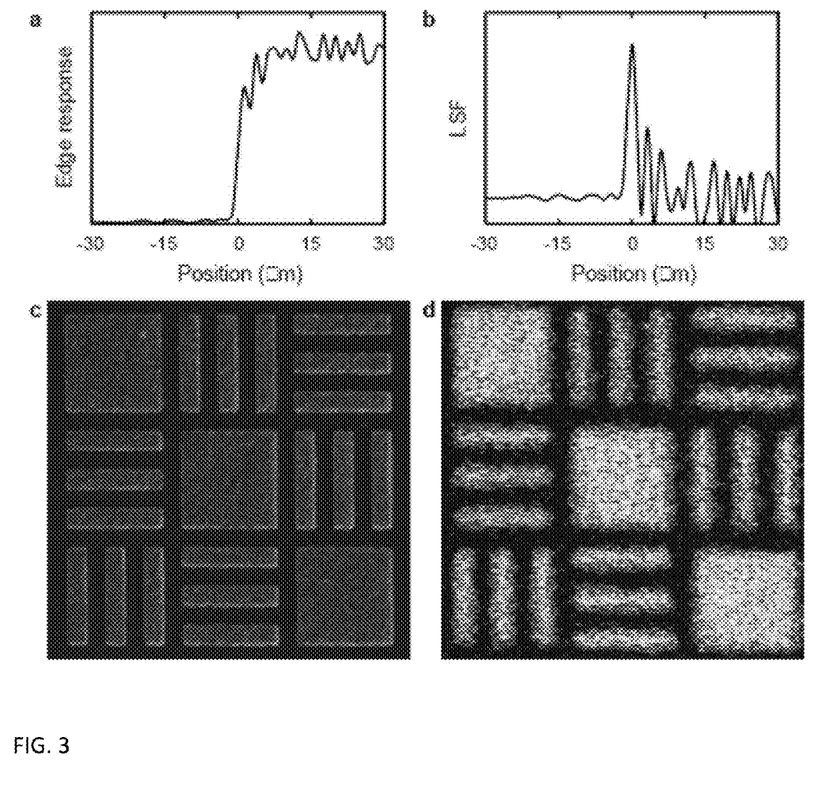
FIG. 3 illustrates various examples of photoacoustic imaging using the transparent transducer.

The polymeric optical resonator illustrated in FIGS. 2a-2f is fabricated on a transparent quartz substrate using a lithography process, for example. The transducer is characterized using the experimental apparatus shown in FIG. 2f. FIG. 3 illustrates various examples of photoacoustic imaging using the transparent transducer.

Figure 4:
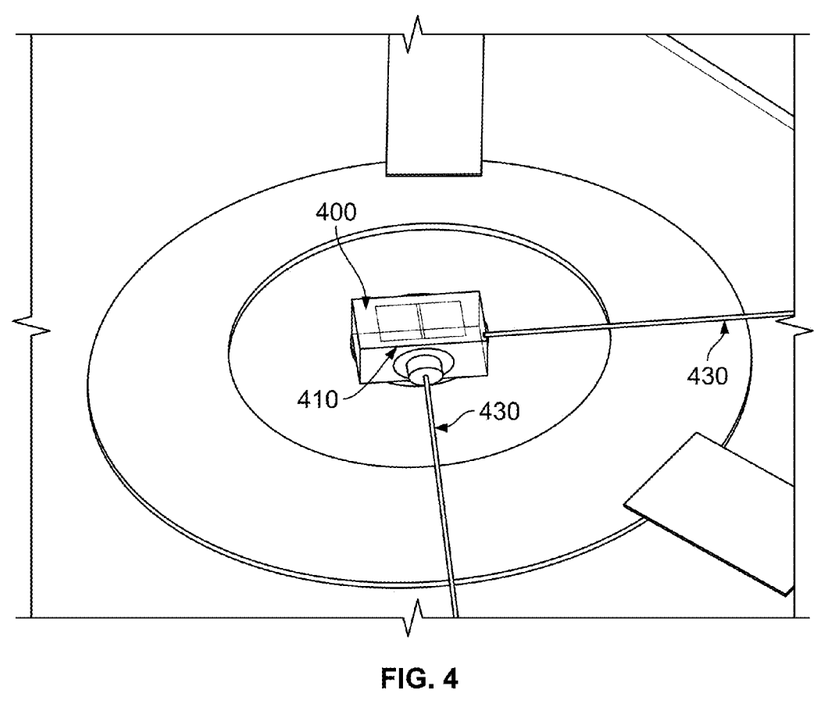
FIG. 4 shows an example transparent transonic transducer fabricated on the conventional microscope cover slide
Figure 5A:
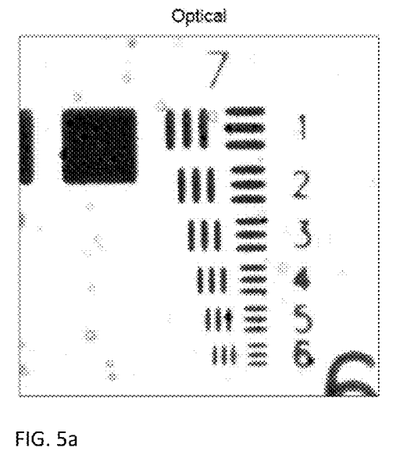
FIGS. 5a-b illustrate simultaneous optical (5a) and photoacoustic (5b) imaging of a target.
Figure 5B:
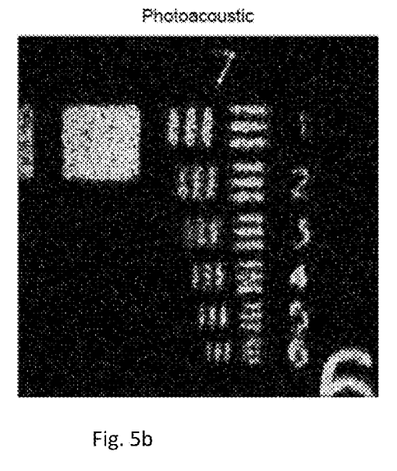

In certain examples, a commercial optical microscope can be converted into a photoacoustic microscope using a transparent ultrasonic transducer. As shown in the example of FIG. 4, a transparent transonic transducer 410 fabricated on the conventional microscope cover slide 400 and connected to one or more optical fibers 420 has a total thickness of less than 500 um and can be further reduced. For example, the transducer can be easily fit onto a microscope sample stage to perform simultaneous (including substantially simultaneous factoring in an operational and/or system delay) optical and acoustic imaging. A low-profile design is compatible with many high numerical aperture (NA) objective lenses to achieve higher imaging resolution. It is compatible with both wide-field and scanning based confocal microscopes without the need to modify the hardware, for example. Particularly, it is possible to simultaneous obtain both optical and photoacoustic imaging, as illustrated, for example, in FIGS. 5a-b.

In certain examples, a reduction in device fabrication cost can be accomplished by developing new scalable micro-/nano-manufacturing process, such as a nano-imprinting or transfer printing process.

In addition, the new fabrication methods also enable fabrication of a flexible ultrasonic transducer by encapsulating a polymeric optical resonator within the transparent and flexible materials. Advantages of using a flexible transducer include: 1) enabling photoacoustic imaging on a non-planar surface, such as on a contact lens for retinal imaging, and 2) enhancing sensitivity by careful designing elastic properties of the optical resonator and the encapsulating flexible materials, for example.

Figure 6:
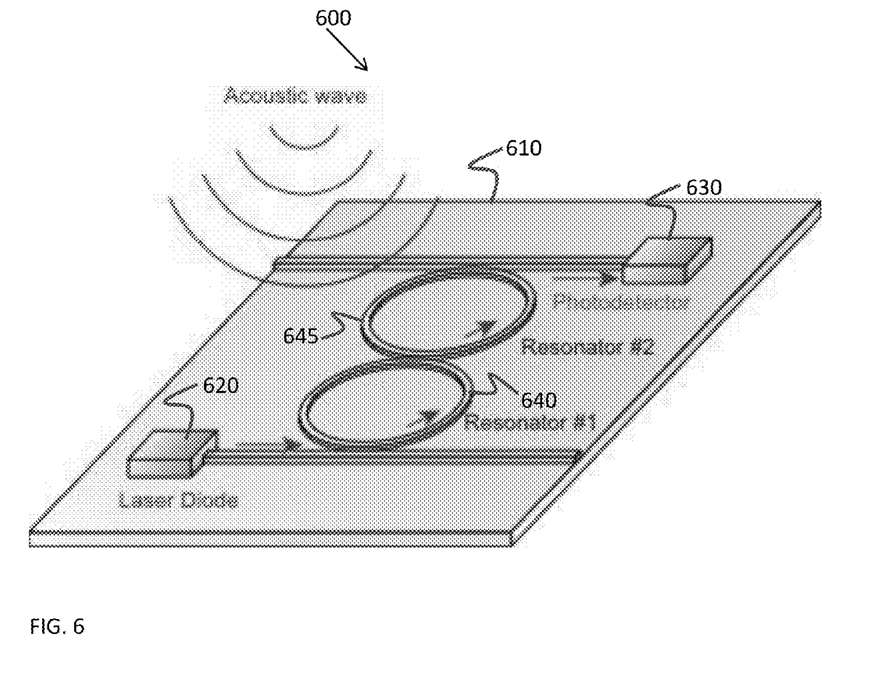
FIG. 6 illustrates an example detector including multiple coupled optical resonators.

Certain examples provide an integrated transparent ultrasonic transducer design. In certain examples, such as the example illustrated in FIG. 6, multiple coupled optical resonators can be combined to enable a low cost, integrated laser source to be used. An example integrated transparent transducer 600, shown in FIG. 6, includes a substrate 610 on which a laser diode 620 and photodetector 630 are positioned with respect to two optical ring resonators 640, 645 (resonator #1 and resonator #2), which are arranged to receive an acoustic wave. As illustrated in FIG. 6, resonators #1 640 and #2 645 can be fabricated using materials with different elastic properties, which provide a difference in mode shift subject to a same pressure wave. Interference between photonic resonance modes from resonator #1 640 and #2 645 is detected using the on-chip photodetector 630. The resonators 640, 645 can be integrated either vertically or laterally, for example. Additional resonators can be added to 1) further improve a signal-to-noise ratio (SNR) of a detected ultrasound signal and 2) serve as an on-board reference to compensate for influence from ambient conditions, such as temperature, and variation in dimension due to fabrication imperfections, for example.

While an example manner of implementing a transparent ultrasonic transducer is illustrated in FIGS. 1, 2, 4, and 6, one or more of the elements, processes and/or devices illustrated in FIGS. 1, 2, 4, and 6 may be combined, divided, re-arranged, omitted, eliminated and/or implemented in any other way. Further, the example elements, processes and devices illustrated in FIGS. 1, 2, 4, and 6 may be implemented by hardware, software, firmware and/or any combination of hardware, software and/or firmware. Thus, for example, any of the example elements, processes and devices illustrated in FIGS. 1, 2, 4, and 6 can be implemented by one or more circuit(s), programmable processor(s), application specific integrated circuit(s) (ASIC(s)), programmable logic device(s) (PLD(s)) and/or field programmable logic device(s) (FPLD(s)), etc. When reading any of the apparatus or system claims of this patent to cover a purely software and/or firmware implementation, at least one of the example elements, processes and devices illustrated in FIGS. 1, 2, 4, and 6 is hereby defined to include a tangible computer readable storage device or storage disc such as a memory, DVD, CD, Blu-ray, etc. storing the software and/or firmware. Further still, the example elements, processes and devices illustrated in FIGS. 1, 2, 4, and 6 may include one or more elements, processes and/or devices in addition to, or instead of, those illustrated in FIGS. 1, 2, 4, and 6, and/or may include more than one of any or all of the illustrated elements, processes and devices.

In certain examples, machine readable instructions can be provided to drive, implement, process, and/or otherwise assist with operation of the transducers described and disclosed herein. In an example, machine readable instructions include a program for execution by a processor such as the processor 712 shown in the example processor platform 700 discussed below in connection with FIG. 7. The program may be embodied in software stored on a tangible computer readable storage medium such as a CD-ROM, a floppy disk, a hard drive, a digital versatile disk (DVD), a Blu-ray disk, or a memory associated with the processor 712, but the entire program and/or parts thereof could alternatively be executed by a device other than the processor 712 and/or embodied in firmware or dedicated hardware. Further, many other methods of implementing the example apparatus and systems described herein may alternatively be used. For example, an order of execution of program components may be changed, and/or some of the elements described may be changed, eliminated, or combined.

As mentioned above, coded instructions (e.g., computer and/or machine readable instructions) can be stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals. As used herein, "tangible computer readable storage medium" and "tangible machine readable storage medium" are used interchangeably. Additionally or alternatively, coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable device or disc and to exclude propagating signals. As used herein, when the phrase "at least" is used as the transition term in a preamble of a claim, it is open-ended in the same manner as the term "comprising" is open ended.

Figure 7:
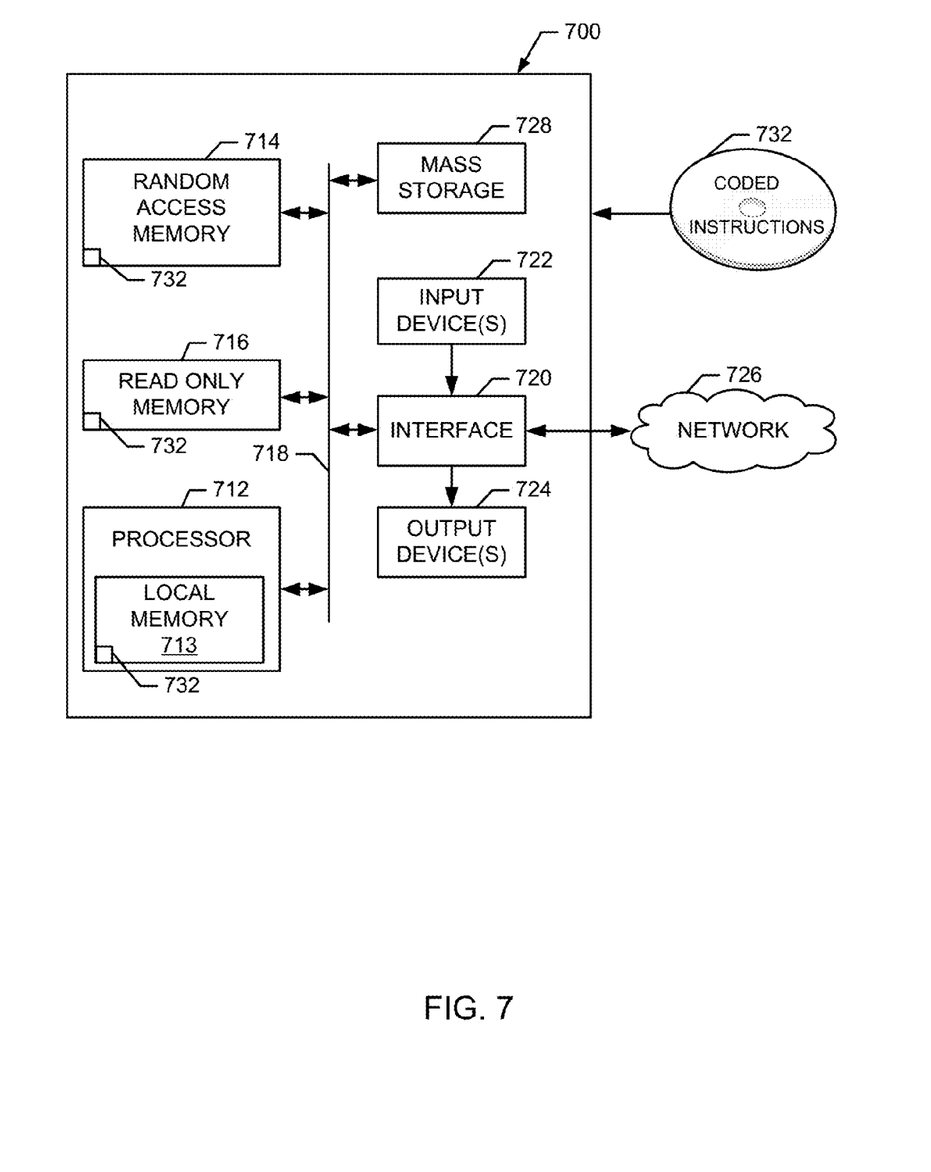
FIG. 7 is a block diagram of an example processor platform capable of executing instructions associated with any or all of FIGS. 1-6.

FIG. 7 is a block diagram of an example processor platform 1000 capable of executing instructions associated with any or all of FIGS. 1-6. The processor platform 700 can be, for example, a server, a personal computer, a mobile device (e.g., a cell phone, a smart phone, a tablet such as an IPAD™), a personal digital assistant (PDA), an Internet appliance, a DVD player, a CD player, a digital video recorder, a Blu-ray player, a gaming console, a personal video recorder, a set top box, or any other type of computing device.

The processor platform 700 of the illustrated example includes a processor 712. The processor 712 of the illustrated example is hardware. For example, the processor 712 can be implemented by one or more integrated circuits, logic circuits, microprocessors or controllers from any desired family or manufacturer.

The processor 712 of the illustrated example includes a local memory 713 (e.g., a cache). The processor 712 of the illustrated example is in communication with a main memory including a volatile memory 714 and a non-volatile memory 716 via a bus 718. The volatile memory 714 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 716 may be implemented by flash memory and/or any other desired type of memory device. Access to the main memory 714, 716 is controlled by a memory controller.

The processor platform 700 of the illustrated example also includes an interface circuit 720. The interface circuit 720 may be implemented by any type of interface standard, such as an Ethernet interface, a universal serial bus (USB), and/or a PCI express interface.

In the illustrated example, one or more input devices 722 are connected to the interface circuit 720. The input device(s) 722 permit a user to enter data and commands into the processor 712. The input device(s) can be implemented by, for example, an audio sensor, a microphone, a camera (still or video), a microscope, a keyboard, a button, a mouse, a touchscreen, a track-pad, a trackball, isopoint and/or a voice recognition system.

One or more output devices 724 are also connected to the interface circuit 720 of the illustrated example. The output devices 724 can be implemented, for example, by display devices (e.g., a light emitting diode (LED), an organic light emitting diode (OLED), a liquid crystal display (LCD), a cathode ray tube display (CRT), a touchscreen, a tactile output device, a light emitting diode (LED), a printer and/or speakers). The interface circuit 720 of the illustrated example, thus, typically includes a graphics driver card.

The interface circuit 720 of the illustrated example also includes a communication device such as a transmitter, a receiver, a transceiver, a modem and/or network interface card to facilitate exchange of data with external machines (e.g., computing devices of any kind) via a network 726 (e.g., an Ethernet connection, a digital subscriber line (DSL), a telephone line, coaxial cable, a cellular telephone system, etc.).

The processor platform 700 of the illustrated example also includes one or more mass storage devices 728 for storing software and/or data. Examples of such mass storage devices 728 include floppy disk drives, hard drive disks, compact disk drives, Blu-ray disk drives, RAID systems, and digital versatile disk (DVD) drives.

Coded instructions 732 may be stored in the mass storage device 728, in the volatile memory 714, in the non-volatile memory 716, and/or on a removable tangible computer readable storage medium such as a CD or DVD.

From the foregoing, it will appreciate that the above disclosed methods, apparatus and articles of manufacture provide improved ultrasonic transducers and improved detection and translation of acoustic emission into optical and/or acoustic image information.

Thus, certain embodiments provide a miniaturized, optically transparent, "coverslip"-type ultrasonic detector based on polymeric MRR. In certain examples, the detector has a high sensitivity, a low noise-equivalent pressure (NEP), a larger sensitivity angle, and an ultra-broad linear frequency bandwidth (e.g., from DC to 140 MHz). The detector also provides improved axial resolution and a higher PA saturation limit for functional PAM. To further enhance imaging performance, better sensitivity of the MRR detector can be obtained by using relatively softer materials to increase the pressure-induced effective RI change of the waveguide and increase the Q-factor of the MRR. The Q-factor can also be improved by using materials with a lower optical absorption coefficient to reduce propagation loss, and/or by introducing onsite re-flow technology to smooth the waveguide surface and hence suppress scattering loss, for example.

Using the transparent MRR detector with a broad range of imaging modalities, such as confocal fluorescence microscopy, optical coherence tomography, and miniaturized fiber optic endoscopy, etc., enables PAM to be used in additional areas such as for cancer research, neuroscience, ophthalmology, etc. In certain examples, MRR detectors can be mass-manufactured and fabricated on various substrates, including flexible plastic film. MRR offers a promise for flexible and disposable ultrasonic detectors for use in endoscopy, ophthalmoscopy, brain imaging, cancer diagnostic imaging, skin imaging, etc. For example, an MRR can be implemented in a microscope cover slide, which can be used alone and/or can be integrated with another clinical optical medical imaging system for endoscopic, ophthalmic, and/or cancer imaging through an independent and/or add-on photoacoustic imaging modality.

Although certain example methods, apparatus and articles of manufacture have been described herein, the scope of coverage of this patent is not limited thereto. On the contrary, this patent covers all methods, apparatus and articles of manufacture fairly falling within the scope of the claims of this patent.

The invention claimed is:

1. A transparent ultrasonic transducer comprising:
a transparent substrate; and
a transparent optical resonator positioned on the transparent substrate, the transparent optical resonator to facilitate excitation of a biological sample and to receive acoustic emission from the biological sample triggered by the excitation,
wherein the transducer is coupled with an optical imaging instrument to facilitate optical and acoustic imaging of the biological sample, and wherein the optical imaging instrument comprises an optical microscope, and wherein the coupling of the transducer with the optical microscope converts the microscope into a photoacoustic microscope for simultaneous optical and acoustic imaging.

2. The transducer of claim 1, further comprising a plurality of optical resonators coupled on the transparent substrate.

3. The transducer of claim 1, further comprising a laser diode and a photodetector arranged with respect to the optical resonator.

4. The transducer of claim 1, wherein the optical resonator comprises a transparent ring optical resonator.

5. The transducer of claim 4, wherein the optical resonator comprises a polymeric optical resonator.

6. The transducer of claim 4, wherein the optical resonator comprises a micro-ring resonator.

7. The transducer of claim 1, further comprising a waveguide coupled to the transparent optical resonator.

8. The transducer of claim 7, further comprising a plurality of optical fibers to couple light in and out of the waveguide.

9. The transducer of claim 7, further comprising a low-dielectric gap between the transparent optical resonator and the waveguide.

10. The transducer of claim 1, wherein the transparent substrate comprises a quartz substrate.

11. The transducer of claim 10, wherein the transparent substrate comprises a non-crystallized fused quartz substrate.

12. The transducer of claim 1, wherein the transparent substrate and the transparent optical resonator are arranged on a microscope cover slide.

13. A ring resonator ultrasonic detector comprising:
a microscope cover slide comprising:
a substrate; and
a ring optical resonator positioned on the substrate, the ring optical resonator to facilitate illumination of a biological sample and to receive acoustic emission from the biological sample in response to the illumination,
wherein the microscope cover slide is coupled with an optical microscope to facilitate optical and acoustic imaging of the biological sample by converting the optical microscope into a photoacoustic microscope for optical and acoustic imaging.

14. The detector of claim 13, further comprising a plurality of optical resonators coupled on the substrate.

15. The detector of claim 13, further comprising a waveguide coupled to the ring optical resonator.

16. The detector of claim 15, further comprising a plurality of optical fibers to couple light in and out of the waveguide.

17. The detector of claim 15, further comprising a low-dielectric gap between the transparent optical resonator and the waveguide.

* * * * *